(12) United States Patent
Souza

(10) Patent No.: US 8,251,076 B2
(45) Date of Patent: Aug. 28, 2012

(54) ORAL HYGIENE CASE WITH DENTAL FLOSS LID COMPARTMENT

(76) Inventor: Nilson Altair de Souza, Curitiba (BR)

(*) Notice: Subject to any disclaimer, the term of this patent is extended or adjusted under 35 U.S.C. 154(b) by 12 days.

(21) Appl. No.: 12/745,867

(22) PCT Filed: Nov. 14, 2008

(86) PCT No.: PCT/BR2008/000350
§ 371 (c)(1),
(2), (4) Date: Jul. 7, 2010

(87) PCT Pub. No.: WO2009/062278
PCT Pub. Date: May 22, 2009

(65) Prior Publication Data
US 2010/0269850 A1    Oct. 28, 2010

(30) Foreign Application Priority Data
Nov. 14, 2007 (BR) .................................... 0704759

(51) Int. Cl.
| | |
|---|---|
| A45D 44/18 | (2006.01) |
| A45D 40/24 | (2006.01) |
| A45D 27/22 | (2006.01) |
| A61C 15/00 | (2006.01) |
| B65D 1/24 | (2006.01) |
| B65D 1/36 | (2006.01) |
| B65D 25/04 | (2006.01) |
| B65D 57/00 | (2006.01) |
| B65D 85/00 | (2006.01) |
| B65D 69/00 | (2006.01) |
| B65D 71/00 | (2006.01) |
| B65D 83/10 | (2006.01) |
| A61B 19/02 | (2006.01) |

(52) U.S. Cl. ........ 132/309; 132/324; 132/314; 132/315; 220/522; 206/581; 206/63.5; 206/362.2; 206/225

(58) Field of Classification Search ............ 132/309, 132/286, 295, 297, 308, 310, 312, 313, 314, 132/315, 317, 318, 321, 323–325, 329; 206/63.5, 206/368, 369, 385, 581, 277, 470, 471, 499, 206/509, 361, 362.2, 225; 220/263, 267, 220/278, 8, 522, 521, 819, 818, 817, 834, 220/833; 222/523, 192, 93, 106; 215/328, 215/384; 221/303, 304, 306, 309, 65
See application file for complete search history.

(56) References Cited

U.S. PATENT DOCUMENTS

| | | | | |
|---|---|---|---|---|
| 1,454,429 A | * | 5/1923 | Dresser | 242/138 |
| 1,858,134 A | * | 5/1932 | Booth et al. | 132/286 |
| 2,049,900 A | * | 8/1936 | Evans et al. | 222/488 |
| 2,458,063 A | * | 1/1949 | Dulberg | 132/314 |
| 2,527,931 A | * | 10/1950 | Iskoe | 15/167.1 |
| 3,890,986 A | * | 6/1975 | Gerlich | 132/309 |
| 4,428,389 A | * | 1/1984 | Sanchez Cordero | 132/325 |
| 4,666,037 A | * | 5/1987 | Weissman | 206/63.5 |

(Continued)

*Primary Examiner* — Vanitha Elgart
(74) *Attorney, Agent, or Firm* — Renner Kenner Greive, Bobak Taylor & Weber

(57) ABSTRACT

Oral hygiene case with dental floss lid compartment, refers to the present invention an improved case with lid compartment to hold dental floss or ribbon, and for keeping a toothbrush or toothpaste in its body that presents constructivity and advanced design with access to the cases body (1) interior concomitant with opening the dental floss lid compartment (2) for use, presents also length and intern volume flexibility, accessories to hang, allowing change of its shape, saving the use of pollutant materials, showing excellent cost-benefit ratio.

3 Claims, 6 Drawing Sheets

U.S. PATENT DOCUMENTS

| | | | | |
|---|---|---|---|---|
| 4,796,783 A * | 1/1989 | Paulson | .................... | 222/80 |
| 4,827,951 A * | 5/1989 | Grussmark | .................... | 132/314 |
| 4,866,809 A * | 9/1989 | Pelletier | .................... | 15/167.1 |
| 5,415,187 A * | 5/1995 | Heneveld | .................... | 132/325 |
| 5,607,050 A * | 3/1997 | Dolan et al. | .................... | 206/63.5 |
| 5,701,921 A * | 12/1997 | Father et al. | .................... | 132/309 |
| 5,732,722 A * | 3/1998 | Mortvedt | .................... | 132/325 |
| 5,832,940 A * | 11/1998 | Embry et al. | .................... | 132/309 |
| 6,412,652 B1 * | 7/2002 | Woram et al. | .................... | 220/521 |
| 6,484,732 B1 * | 11/2002 | Simister | .................... | 132/309 |
| 6,497,236 B1 * | 12/2002 | Yates et al. | .................... | 132/309 |
| 6,526,991 B2 * | 3/2003 | Bodwalk | .................... | 132/309 |
| 6,568,529 B2 * | 5/2003 | McMurrey | .................... | 206/385 |
| 6,675,815 B1 * | 1/2004 | Hofstad | .................... | 132/309 |
| 6,782,999 B1 * | 8/2004 | McCoy et al. | .................... | 206/223 |
| 6,895,628 B1 * | 5/2005 | Anderson | .................... | 15/106 |
| 7,011,467 B1 * | 3/2006 | Fiore et al. | .................... | 401/278 |
| 7,243,663 B1 * | 7/2007 | Einstein et al. | .................... | 132/314 |
| 7,267,126 B1 * | 9/2007 | Banegas | .................... | 132/309 |
| 7,942,155 B2 * | 5/2011 | Van Iderstine | .................... | 132/309 |
| 2002/0088474 A1 * | 7/2002 | Montalvo | .................... | 132/309 |
| 2002/0100490 A1 * | 8/2002 | Bodwalk | .................... | 132/309 |
| 2005/0211263 A1 * | 9/2005 | Kuo | .................... | 132/310 |
| 2006/0225766 A1 * | 10/2006 | Iderstine | .................... | 132/322 |
| 2010/0108676 A1 * | 5/2010 | Salciarini et al. | .................... | 220/263 |
| 2010/0230570 A1 * | 9/2010 | Vosbikian et al. | .................... | 248/311.2 |

\* cited by examiner

ORAL HYGIENE CASE WITH DENTAL FLOSS LID COMPARTMENT

FIELD OF INVENTION

The present invention refers to a totally new case with a compartment to hold dental floss or ribbon attached to the lid, and for keeping a toothbrush or toothpaste in its body that presents a constructive and advanced design. The case features an access to the case's interior concomitant with opening the dental floss housing for use, length and intern volume flexibility, accessories to hang, aiming being different on the major concept which is reducing packing size of the dental floss or ribbon, paste and brush products, specially by changing the paradigm that people don't have the habit of carrying those, allowing change of its shape, saving the use of pollutant materials, and showing excellent cost-benefit ratio.

BACKGROUND OF THE INVENTION

As it's of knowledge of the technicians responsible for manufacturing cases for oral hygiene products, the first cases to be developed would hold toothbrush, toothpaste, dental ribbon or floss arranged loose or fit in the case. Among others, the Brazilian patents MU7800574-4, MU8202290-9 and MU8500729-3, of the same inventor of the present invention, revealed improved cases with the same concept of the first cases, but still those bring inconveniences and difficulties of use, using many high priced items that also produce non-biodegradable industrial residues.

After researching, carrying cases were found as shown on the following patents:

a) The US patent Des. 328,978, that presents integrated dental floss on one of the case's extremities, and internal space for toothbrush combined with another lid, with a single lid for accessing the case's interior, with space only for the toothbrush and the dental floss is fixed on the other end of the case's body;

b) US patent Des. 336,782, that presents carrying case combining toothbrush, toothpaste compartment, dental floss holder and protecting dental floss cover on the same shape as the case, without internal space for accommodating items and with fixed compartment for dental floss on one of the body's extremity;

c) U.S. Pat. No. 5,078,526 presents tube shaped case for accommodating dental paste and brush, with inferior end for fitting dental floss holder and lid together with prismatic square duct for housing the toothpaste, with no internal space for accommodating items and with fixed dental floss on one of the body's extremity;

d) US patent Des, 362,341, presents prismatic rectangular case, with space for accommodating toothbrush with its cover and a compartment for dental floss on the opposite side, with no internal space for accommodating items and with fixed dental floss on one of the case's body extremity;

e) U.S. Pat. No. 5,415,187 presents prismatic rectangular case combining compartment for dental floss on one of its ends, space for toothbrush and its cover in the centre, and room for the toothpaste on the other end of the case, without internal space for accommodating items and with dental floss fixed on one of the body's extremity;

f) Patent US2002088474 shows prismatic case accommodating the dental floss on one of its ends, space for toothbrush and its cover in the centre and the toothpaste on the other end, with no internal space for accommodating items and with a fixed dental floss on one of the body's end;

g) Patent US2005211263 presents toothbrush container with torsion and ventilating cover integrated with the dental floss compartment, with room for toothbrush with dental paste compartment and with a lid on one of its ends and with fixed dental floss section on the other end, with no internal space for accommodating items and with fixed dental floss on one of its body's extremity;

h) Patent US2006260635 presents case combining toothbrush, and dental floss compartment on its opposite end, with no internal space for accommodating items and with dental floss compartment on one of the case's body extremity;

i) Patent US2006280548 presents a lid with dental floss compartment on its toothbrush's extremity, without internal space for accommodating items and with fixed dental floss compartment on one of the case's body extremity;

j) Patent US2007110503 shows a case including space for toothbrush and accommodation of dental floss on the opposite side, with no internal space for accommodating items and with dental floss compartment on one of the case's body extremity.

The carrying cases revealed previously show disadvantages and limitations of having restrict space and only accommodating toothbrush with or without dental paste compartment, and of using a single access lid to the case's interior and also the fact that the dental floss compartment does not open and give access the case's interior.

BRIEF SUMMARY OF THE INVENTION

ORAL HYGIENE CASE WITH LID COMPARTMENT FOR DENTAL FLOSS OR RIBBON, object of the present patent was developed to overcome the limitations and disadvantages of the current kits, due to its totally new constructivity and design, with access to the case's interior concomitant with the opening of the dental floss compartment for use, length and internal volume case's flexibility, with accessories to hang, allowing change of its shape, saving the use of pollutant materials, showing excellent cost-benefit ratio. Additionally, presents the advantages of flexibility to store brush and pastes of all sizes and weights, adopting packing size reduction for transport and sales, providing consequent environment control, minimizing the use of contaminating materials for the environment and, of being able to carry advertisements on the case's body.

Obtaining the optimized carrying case of the present patent demanded incessant technical research and searches for technologies, aiming being different on the major concept which is reducing packing size of the dental floss or ribbon, paste and brush products specially by changing the paradigm that people don't have the habit of carrying those. Therefore this invention intends to facilitate the creation of such habit, of carrying their dental supplies in a practical way, reducing packing which contaminates the environment.

For better understanding of the present patent, the following figures were attached containing one of the possible constructive forms:

DETAILED DESCRIPTION OF THE INVENTION

Figure 1:
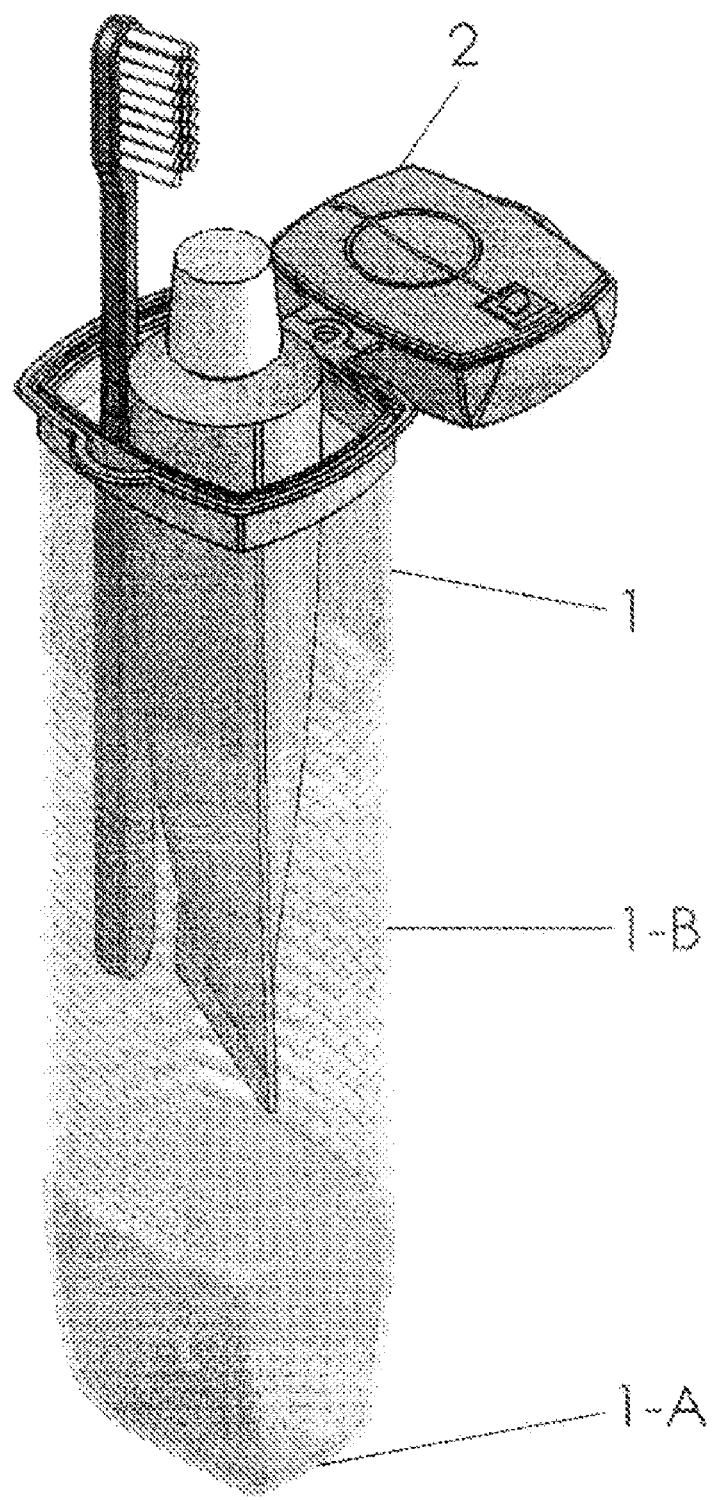
FIG. 1., shows the case's frontal section perspective of the present patent, with the compartment for dental floss opened, and with the toothbrush and paste being taken off the case.
Figure 2:
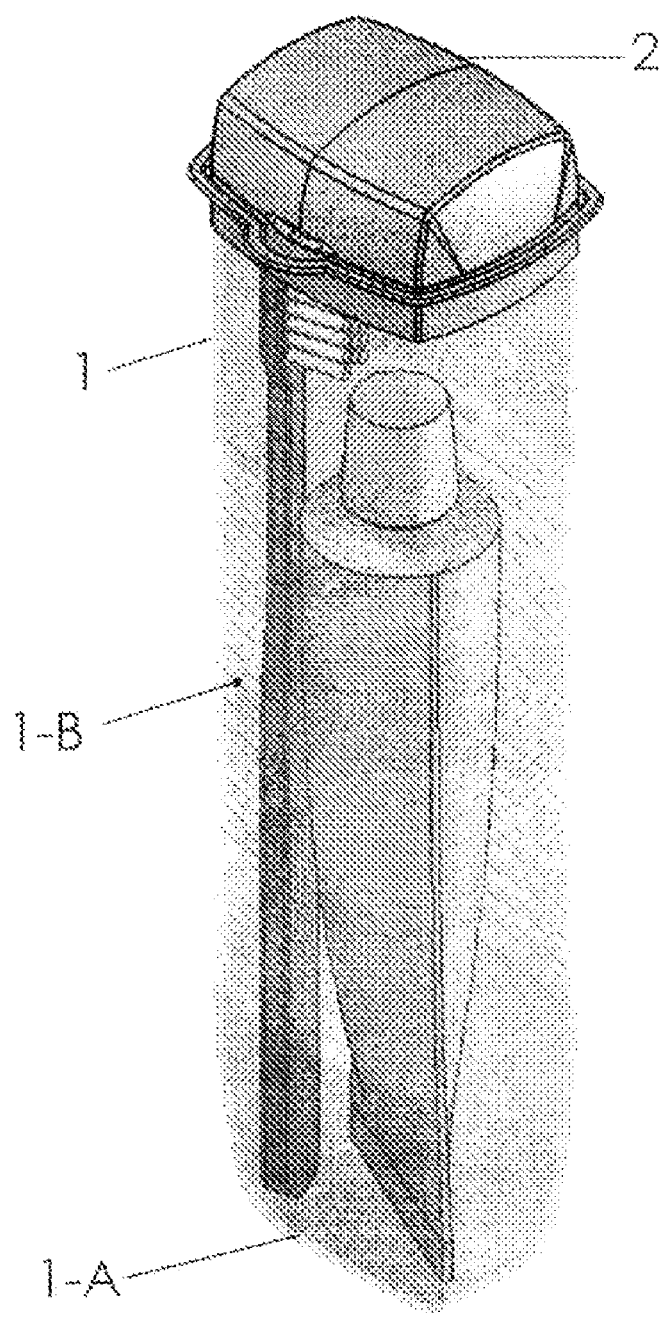
FIG. 2., shows the case's frontal section perspective of the present patent, with the dental floss compartment closed and the toothbrush and paste placed in its interior.
Figure 3:
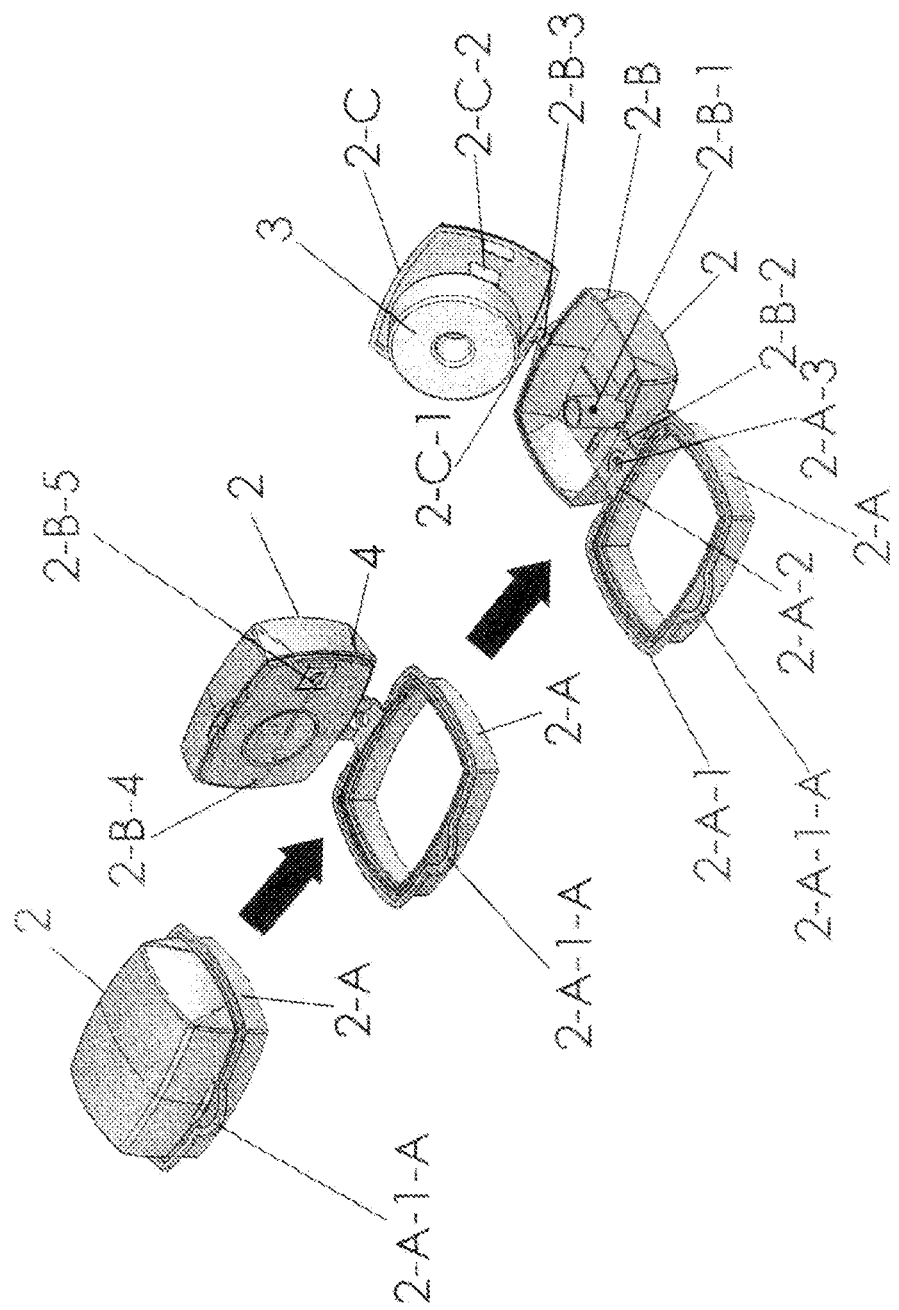
FIG. 3., shows a frontal perspective of the lid compartment of the present invention, when closed, when opened for use of the dental floss and opened for use of the case's interior, and also of the lid compartment when disassembled for switching the dental floss roll.
Figure 4:
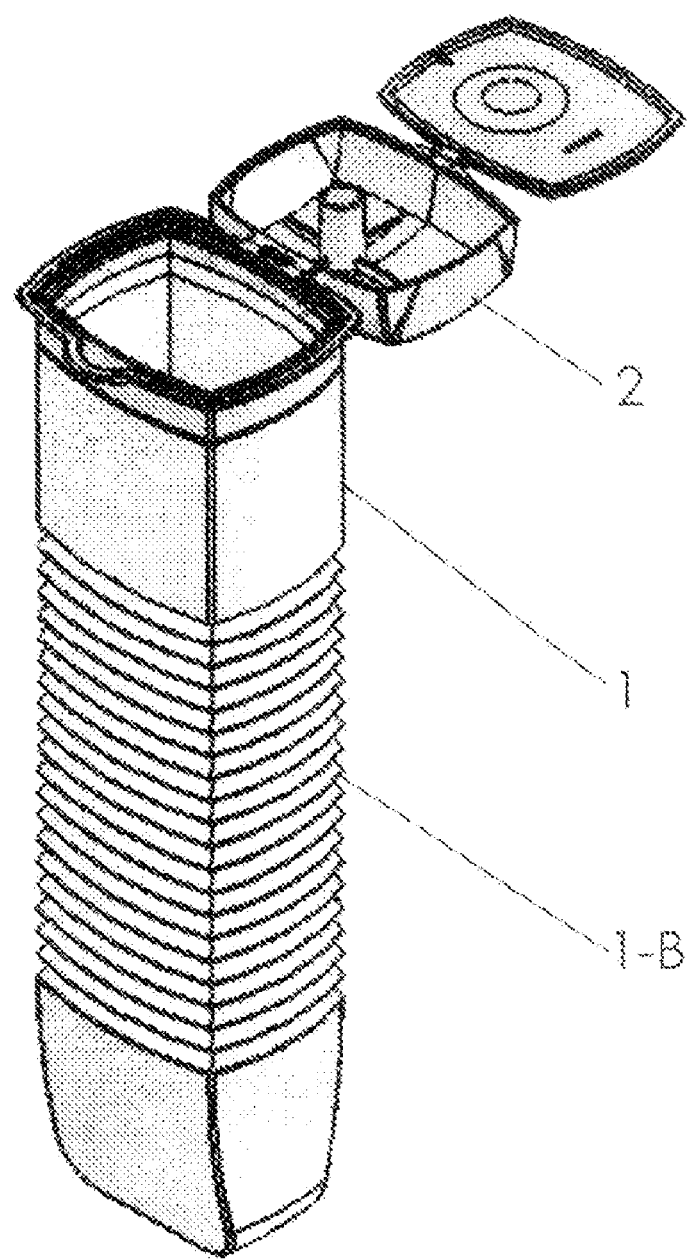
FIG. 4., shows a frontal view of the case's body of the present patent, with the dental floss lid compartment opened, with no dental floss roll in it.
Figure 5:
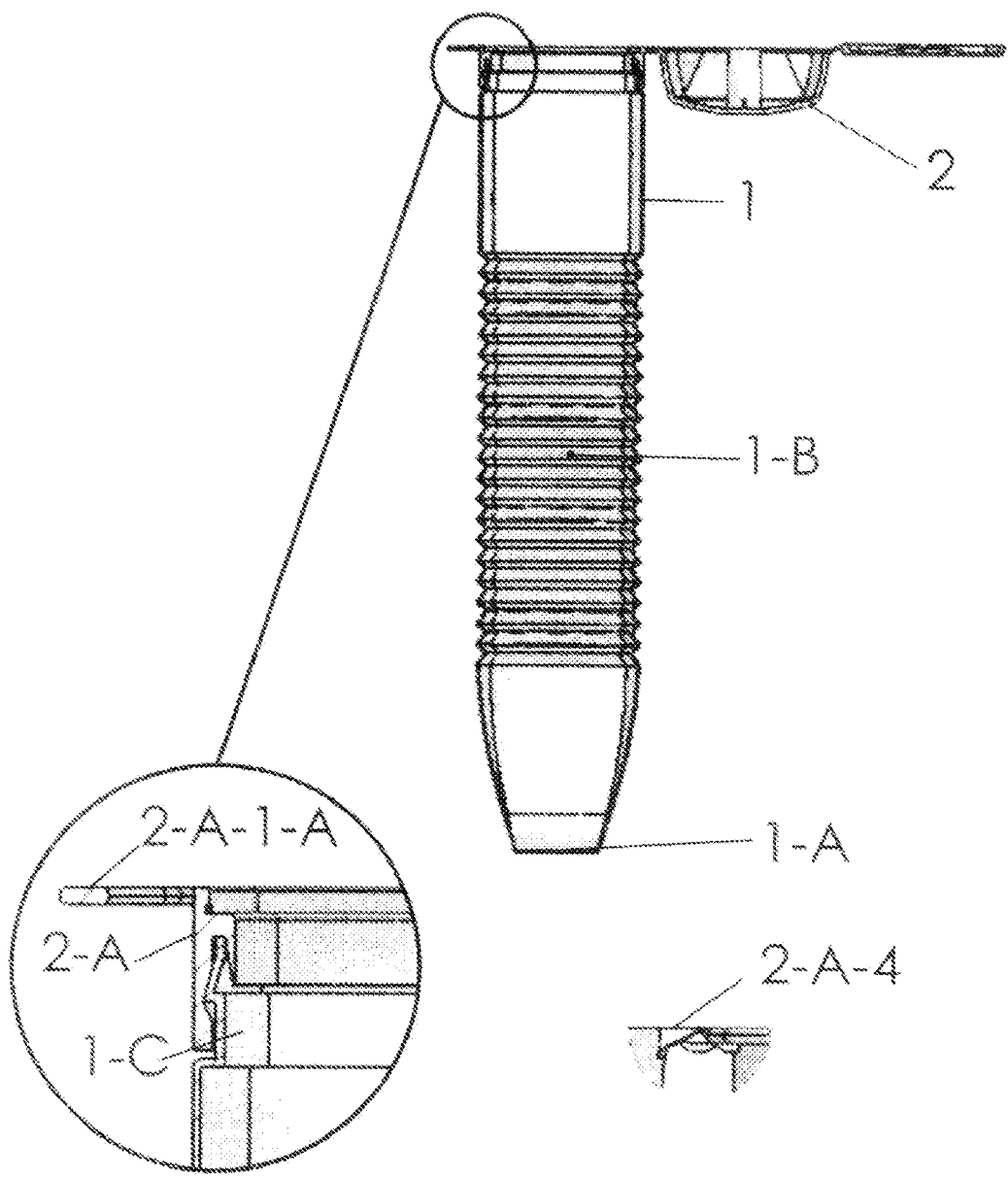
FIG. 5., shows a transversal section view of the case of the present patent with detailed connection of body and lid compartment.
Figure 6:
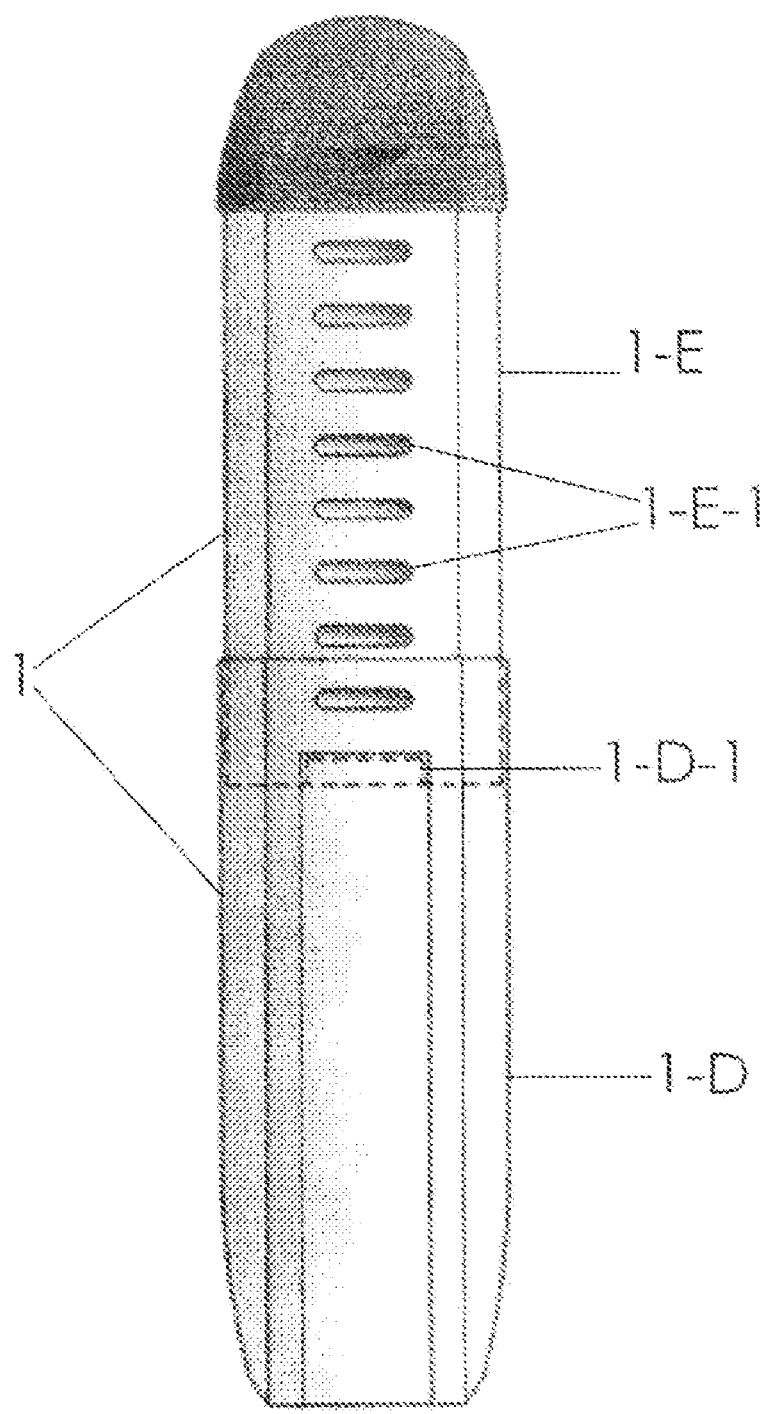
FIG. 6., shows a side view of the case's body of the present patent with the possibility to vary the volume by locks and by lowering height.

According to the referred figures, the improved case of the present patent includes body (1) of polygonal prismatic shape or cylindrical, or mixed, with lower part (1-A) closed or with conventional lid, central part with room for advertising and with folding (1-B) and the superior part with spread mouth (1-C) and with compatible dimension and section with the body (1), dental floss lid compartment (2) of compatible dimension and section with the case's body (1) with a frame (2-A) with compatible shape, that fits the mouth (1-C) by means of the lock (2-A-4) and containing ring (2-A-1) with handle (2-A-1-A) and flap (2-A-2) with opening (2-A-3) to make a hinge with flap (2-B-2), base (2-B) of polygonal prismatic shape or cylindrical or mixed, with its bottom closed and the top opened including a fitting spool tube (2-B-1) fixed on its centre, flap (2-B-2) to make a hinge with the flap (2-A-2), flap (2-B-3) connected to flap (2-C-1), opening for dental floss crossing (2-B-4) and opening (2-B-5) for fitting the knife (4), lid (2-C) with compatible shape with the base (2-B) with flap (2-C-1) connected to flap (2-B-3), two guides (2-C-2) laterally placed inside the case, conventional spool (3) and conventional knife (4).

As an alternative, the body (1) can be divided in two parts: anterior part (1-D) with bigger transversal section than the transversal section of the posterior part (1-E) containing a lock (1-D-1) and posterior part (1-E) containing height adjusters (1-E-1) that fit each other, allowing variation of the case's internal volume.

The case can be used as described bellow:

1. For keeping objects:
   1.a. The dental floss lid compartment (2) is opened allowing the access to the case's body interior (1);
   1.b. The length of the case can be regulated by the folding (1-B) in order to keep the toothbrush, paste or another objects;
   1.c. The dental floss lid compartment is closed.

2. For taking objects off it and using them:
   2.a. The dental floss lid compartment (2) is opened, accessing the case's body interior (1);
   2.b. The dental floss can be pulled from the dental floss lid compartment (2) and cut for use;
   2.c. The toothbrush, paste or any other object can be taken off the case for use;
   2.d. Once finished using them, the objects can be kept in the case, the dental floss lid compartment (2) can be closed, and hanged or not by its handle (2-A-1-A) or by the opening (2-A-3);

The invention claimed is:

1. An oral hygiene case with a dental floss lid compartment characterized by a body having a polygonal prismatic shape wherein the body includes an anterior part and a separate posterior part, wherein the anterior part has a larger cross section than the posterior part and contains a lock, wherein the posterior part contains a plurality of height adjusters that fit the lock so as to allow an internal volume of the case to be varied depending upon which height adjuster of the posterior part is fitted with the lock of the anterior part, and wherein the posterior part has an open mouth; and a dental floss lid compartment having a shape compatible with the shape of the body, the dental floss lid compartment including (a) a frame having compatible dimensions and a cross section so as to compatibly fit into the mouth of the posterior part of the body and capable of being retained therein by means of a locking mechanism, the frame containing a ring, said ring having a handle and a flap therein to make a hinge; (b) a base having a shape compatible to the frame and having a closed bottom and an open top, the base further including a fitted spool tube affixed centrally in the base and a first flap compatible with the flap of the frame to make the hinge, and a second flap located generally opposite the first flap; and (c) a lid with a compatible shape to the base, the lid having an opening for dental floss dispensing and an opening for a knife, wherein a side of the lid to be enclosed within the base includes two guides laterally placed thereon and a spool for holding dental floss and wherein the lid includes a flap connected to the second flap of the base to make a second hinge.

2. An oral hygiene case with a dental floss lid compartment characterized by
a body having a polygonal prismatic shape wherein the body includes (i) a lower part having a closed end, the closed end optionally being closed with an openable lid, (ii) a central part having space suitable for advertising indicia and a plurality of convolutional folds and (iii) an upper part with an open mouth having dimensions and a cross section comparable to the center part of the body; and a dental floss lid compartment having a shape compatible with the shape of the body, the dental floss lid compartment including (a) a frame having compatible dimensions and a cross section so as to compatibly fit into the mouth of the upper part of the body and capable of being retained therein by means of a locking mechanism, the frame containing a ring, said ring having a handle and a flap therein to make a hinge, wherein at least one of the handle and the flap has an opening suitable for use in hanging the case; (b) a base having a shape compatible to the frame and having a closed bottom and an open top, the base further including a fitted spool tube affixed centrally in the base and a first flap compatible with the flap of the frame to make the hinge, and a second flap located generally opposite the first flap; and (c) a lid with a compatible shape to the base, the lid having an opening for dental floss dispensing and an opening for a knife, wherein a side of the lid to be enclosed within the base includes two guides laterally placed thereon and a spool for holding dental floss and wherein the lid includes a flap connected to the second flap of the base to make a second hinge.

3. The oral hygiene case with a dental floss lid compartment, according to claim 1, wherein at least one of the handle and the flap of the frame has an opening suitable for use in hanging the case.

* * * * *